United States Patent
Brito-De-La-Fuente et al.

(10) Patent No.: US 11,612,578 B2
(45) Date of Patent: *Mar. 28, 2023

(54) NUTRITIONAL COMPOSITION FOR USE IN THERAPY OF PATIENTS WITH SARCOPENIA AND/OR FRAILTY OR PRE-SARCOPENIC AND/OR PRE-FRAIL PATIENTS

(71) Applicant: Fresenius Kabi Deutschland GmbH, Bad Homburg (DE)

(72) Inventors: Edmundo Brito-De-La-Fuente, Bad Homburg (DE); Ericka Pestana, Bad Homburg (DE); Stephanie Reichart, Bad Homburg (DE); Maria Fernanda Martinez-Bock, Frankfurt am Main (DE); Sarah Ashley-Maguire, Dorking (GB); Jose Maria Mainou-Sierra, Bad Homburg (DE)

(73) Assignee: FRESENIUS KABI DEUTSCHLAND GMBH, Bad Homburge (DE)

( * ) Notice: Subject to any disclaimer, the term of this patent is extended or adjusted under 35 U.S.C. 154(b) by 519 days.

This patent is subject to a terminal disclaimer.

(21) Appl. No.: 16/461,616

(22) PCT Filed: Nov. 16, 2017

(86) PCT No.: PCT/EP2017/079392
§ 371 (c)(1),
(2) Date: May 16, 2019

(87) PCT Pub. No.: WO2018/091564
PCT Pub. Date: May 24, 2018

(65) Prior Publication Data
US 2020/0061013 A1    Feb. 27, 2020

(30) Foreign Application Priority Data
Nov. 16, 2016   (EP) .................................... 16199106

(51) Int. Cl.
| | |
|---|---|
| *A61K 31/202* | (2006.01) |
| *A61P 21/00* | (2006.01) |
| *A61K 31/05* | (2006.01) |
| *A61K 47/42* | (2017.01) |
| *A61K 47/44* | (2017.01) |
| *A61K 31/197* | (2006.01) |
| *A61K 31/355* | (2006.01) |
| *A61K 31/405* | (2006.01) |
| *A61K 33/06* | (2006.01) |

(52) U.S. Cl.
CPC ............ *A61K 31/202* (2013.01); *A61K 31/05* (2013.01); *A61K 31/197* (2013.01); *A61K 31/355* (2013.01); *A61K 31/405* (2013.01); *A61K 33/06* (2013.01); *A61K 47/42* (2013.01); *A61K 47/44* (2013.01); *A61P 21/00* (2018.01)

(58) Field of Classification Search
CPC .... A61K 31/20; A61K 31/201; A61K 31/202; A61K 31/197; A61K 31/198; A61K 31/355; A61K 31/405; A61K 47/42; A61K 47/44; A61P 21/00; A23L 33/00
See application file for complete search history.

(56) References Cited

U.S. PATENT DOCUMENTS

| | | | | |
|---|---|---|---|---|
| 4,025,650 | A * | 5/1977 | Gans | ..................... A23L 33/175 |
| | | | | 514/801 |
| 5,221,668 | A * | 6/1993 | Henningfield | .......... A23L 33/15 |
| | | | | 514/23 |
| 8,846,759 | B2 | 9/2014 | Luiking et al. | |
| 2004/0087490 | A1* | 5/2004 | Troup | ................ A61K 31/4172 |
| | | | | 514/567 |
| 2007/0098762 | A1* | 5/2007 | Stahl | ....................... A61P 37/00 |
| | | | | 514/54 |
| 2008/0233245 | A1 | 9/2008 | White et al. | |

(Continued)

FOREIGN PATENT DOCUMENTS

| | | |
|---|---|---|
| AU | 607071 B2 | 2/1991 |
| CN | 1034578 C | 4/1997 |

(Continued)

OTHER PUBLICATIONS

Markus et al. "Whey protein rich in α-lactalbumin increases the ratio of plasma tryptophan to the sum of the other large neutral amino acids and improves cognitive performance in stress-vulnerable subjects,"AM J. Clin. Nutr. 2002, vol. 75, pp. 1051-1056 (Year: 2002).*

(Continued)

*Primary Examiner* — Shengjun Wang
(74) *Attorney, Agent, or Firm* — Hylton-Rodic Law PLLC

(57) ABSTRACT

The invention relates to PUFA, vitamin E, vitamin D and the protein bound amino acids glycine, arginine and tryptophan as active ingredients for use in therapy of patients with sarcopenia and/or frailty or pre-sarcopenic and/or pre-frail patients, wherein an effective amount of said active ingredients is administered in the form of a nutritional composition comprising a) a lipid component providing 40-50 EN % based on the total energy of the nutritional composition, wherein 12-16 EN % based on the total energy of the nutritional composition is provided by PUFA, b) 4.0-8.0 mg/100 mL alpha-TE vitamin E, c) 5.0-12.0 μg/100 mL vitamin D, d) 2.5-4.5 g/100 mL glycine, e) 0.5-1.5 g/100 mL arginine, and f) at least 0.02 g/100 mL tryptophan.

5 Claims, No Drawings

(56) References Cited

U.S. PATENT DOCUMENTS

| | | | |
|---|---|---|---|
| 2012/0027897 A1* | 2/2012 | Innocenzi | A23L 33/00 426/231 |
| 2012/0195873 A1* | 8/2012 | Miller | A61K 31/202 424/94.4 |
| 2013/0252899 A1* | 9/2013 | Hausmanns | A23L 33/18 530/356 |

FOREIGN PATENT DOCUMENTS

| | | |
|---|---|---|
| CN | 102647990 A | 8/2012 |
| CN | 102665736 B | 10/2014 |
| CN | 103783532 B | 6/2016 |
| CN | 103079415 B | 8/2016 |
| WO | 2011011252 A1 | 1/2011 |
| WO | 2012005582 A1 | 1/2012 |
| WO | 2012024611 A1 | 2/2012 |
| WO | WO-2012024611 A1 * | 2/2012 ............ A61K 45/06 |
| WO | WO-2014200332 A1 * | 12/2014 ............ A23L 33/19 |

OTHER PUBLICATIONS

Joshi et al. "Vitamin D deficiency in adults," Australian Prescriber, 2010, vol. 33, No. 4, pp. 103-106 (Year: 2010).*

Hardman "Omega-3 Fatty acids to Augment cancer therapy," J. Nutr. 2002, vol. 132, pp. 3508S to 3512S (Year: 2002).*

Matthaus et al. "Some rape/canola seed oils: fatty acid composition and tocopherols," Z. Naturforsch, 2016, 71(3-4)C: 73-77. (Year: 2016).*

* cited by examiner

NUTRITIONAL COMPOSITION FOR USE IN THERAPY OF PATIENTS WITH SARCOPENIA AND/OR FRAILTY OR PRE-SARCOPENIC AND/OR PRE-FRAIL PATIENTS

CROSS REFERENCE TO RELATED APPLICATIONS

This application is a U.S. national stage application of International Application No. PCT/EP2017/079392, filed Nov. 16, 2017, which claims the benefit of the filing date of European Application EP 16199106.2, filed Nov. 16, 2016, the contents of which are hereby incorporated by reference in their entirety.

FIELD OF THE INVENTION

The invention relates to PUFA, vitamin E, vitamin D and the protein bound amino acids glycine, arginine and tryptophan as active ingredients for use in therapy of patients with sarcopenia and/or frailty or pre-sarcopenic and/or pre-frail patients, wherein an effective amount of said active ingredients is administered in the form of a nutritional composition. The invention also relates to the nutritional composition as such.

BACKGROUND OF THE INVENTION

Sarcopenia can be described as the loss of muscle mass and strength, which can lead to physical function impairment. Frailty can be described as a combination of this loss of muscle mass with physical function impairment, which can result in weight loss, fatigue, poor mobility, cognitive impairment and/or social isolation. Sarcopenia can be a major symptom of the frailty syndrome.

Ageing is frequently accompanied by a loss of muscle mass and function resulting from an imbalance between the rates of muscle protein synthesis and muscle protein breakdown. After the age of 40 years, muscle mass (lean body mass) decreases by approximately 8% per decade and this increases to 15% per decade after the age of 70 years.

Loss of muscle mass in elderly people can impact on health, leading to a variety of health and functional problems. As muscle mass is depleted, patients can face a reduction in mobility, both in speed and dexterity. Independence is therefore reduced which can then lead to the patient becoming depressed and isolated. This can then result in a downward spiral ultimately leading to increased mortality. Sarcopenia is therefore a major cause of disability, resulting in diminished quality of life and an increased risk of death.

Sarcopenia can affect all elderly people, overweight, underweight and those of a healthy weight as it is muscle mass/strength loss not total weight loss.

Frailty describes a condition in which multiple body systems gradually lose their in-built reserves. Sarcopenia can be a significant risk factor in the development of frailty and the two can be inextricably linked.

Fried's phenotypic definition of frailty is commonly used as it describes frailty as a syndrome that is recognizable. According to Fried, five clinical manifestations of frailty are defined that are consistent with clinical observations. These are weight loss with or without sarcopenia, exhaustion, weakness, slowness and reduced physical activity. A diagnosis of frailty is made if three or more of the symptoms are identified. If a patient presents with one or two of the above symptoms, then a "pre-frail" diagnosis can be made. Weight loss can be a major component of the frailty syndrome.

Malnutrition and sarcopenia can be the heart of a frailty diagnosis. For example, the vicious cycle begins with the loss of muscle mass combined with disease (e.g. heart disease, diabetes, dementia) which reduces strength and power which subsequently reduces walking speed and increases dependency. Due to these symptoms, mobility and total energy expenditure are reduced. This leads to malnutrition where the downward deteriorating cycle of frailty continues.

The prevalence of frailty increases with age and is higher in women than in men. Elderly people with frailty are at significant risk of sudden and dramatic changes in their physical and mental well-being after a seemingly small event that challenges their health, such as a minor infection or new medication. Falls, delirium and immobility are the usual sudden, dramatic changes observed in frailty. Elderly people with frailty are also at increased long-term risk of disability, hospitalisation, care home admission and mortality.

Due to poor appetite, reduced mobility and isolation, sarcopenic and/or frail people, are often not able to meet their calorie, protein and micronutrient (e.g. vitamin D) requirements with food alone. To ensure these requirements are met, nutritional compositions, in particular oral nutritional compositions, are needed.

Accordingly, there is a need for systems which can be used in therapy of patients with sarcopenia and/or frailty or pre-sarcopenic and/or pre-frail patients. In particular, there is a need for nutritional compositions which provide sufficient amounts of calories, protein and micronutrients (e.g. vitamin D) in a relatively low volume, as sarcopenic and/or frail people do often not tolerate high or even normal volumes of food and/or nutritional compositions. Preferably, such compositions can be adapted to be nutritionally complete.

SUMMARY OF THE INVENTION

The inventors found a system which can be used in therapy of patients with sarcopenia and/or frailty or pre-sarcopenic and/or pre-frail patients. Said system involves the combined use of PUFA, vitamin E, vitamin D and the protein bound amino acids glycine, arginine and tryptophan as active ingredients. The corresponding nutritional compositions provide sufficient amounts of calories, protein and micronutrients (e.g. vitamin D) in a relatively low volume, and they can be adapted to be nutritionally complete.

Accordingly, in a first aspect, the present disclosure relates to PUFA, vitamin E, vitamin D and the protein bound amino acids glycine, arginine and tryptophan as active ingredients for use in therapy of patients with sarcopenia and/or frailty or pre-sarcopenic and/or pre-frail patients, wherein an effective amount of said active ingredients is administered in the form of a nutritional composition comprising a) a lipid component providing 40-50 EN % based on the total energy of the nutritional composition, wherein 12-16 EN % based on the total energy of the nutritional composition is provided by PUFA, b) 4.0-8.0 mg/100 mL alpha-TE vitamin E, c) 5.0-12.0 µg/100 mL vitamin D, d) 2.5-4.5 g/100 mL glycine, e) 0.5-1.5 g/100 mL arginine, and f) at least 0.02 g/100 mL tryptophan.

In a second aspect, the present disclosure relates to the nutritional composition as such.

In a third aspect, the present disclosure relates to a dose unit comprising the nutritional composition.

In a fourth aspect, the present disclosure relates to a dosage regime for use in (nutritional) therapy of patients with sarcopenia and/or frailty or pre-sarcopenic and/or pre-frail patients.

DETAILED DESCRIPTION OF THE INVENTION

Definitions

"High protein" as used herein refers to nutritional compositions wherein the protein component provides at least 15 EN %, preferably at least 18 EN %, more preferably at least 19 EN %, most preferred at least 20 EN % based on the total energy of the nutritional composition. In preferred embodiments, such nutritional compositions comprise at least 10 wt %, preferably at least 12 wt %, more preferably at least 13 wt %, most preferred at least 14 wt % of protein based on the total weight of the nutritional composition. According to the present disclosure, there may be an upper limit to protein content, for example at most 40 EN %, preferably at most 30 EN %, more preferably at most 28 EN %.

"High caloric" as used herein refers to nutritional compositions having a caloric density of at least 2 kcal/mL, preferably at least 2.5 kcal/mL, more preferably at least 2.8 kcal/mL, most preferably at least 3.0 kcal/mL.

"Nutritional composition" herein refers to a synthetically produced food composition. Thus, nutritional compositions are artificial nutritional products obtained by mixing/dissolving bulk ingredients whereby said ingredients are typically provided in solid form (e.g. powders) or liquid from (e.g. oils, water, syrup). The term "nutritional composition" excludes "food", i.e. non-modified natural food products, such as meat, vegetables, fruits in their natural form and conventionally prepared (e.g. cooked) meals or drinks like tea, coffee or juices.

For the present disclosure, "nutritional compositions" are limited to liquid or semi-solid compositions.

"Patient nutrition" as used herein refers to nutrition intended for individuals suffering from a medical condition. Patient nutrition as defined herein excludes the provision of nutrients in the form of conventionally prepared meals ("food"). Patient nutrition therefore only refers to the provision of nutrients in form of nutritional compositions as defined above. Herein, patient nutrition is intended for patients having high caloric needs and high protein needs.

"Nutritionally complete" refers to nutritional compositions suitable as sole source of nutrition. To be nutritionally complete, it is required that a nutritional composition comprises—in addition to the lipid, carbohydrate and protein components—minerals and vitamins. In order to be nutritionally complete, vitamins and minerals should be present in sufficient amounts as known to the man skilled in the art, i.e. in accordance with established nutritional guidelines. The recommended nutrient requirements, in particular with respect to minerals and vitamins, can be found in standard nutritional guidelines such as EU commission directive 1999/21/EC (see tables 2 and 3 hereinbelow). Suitable nutrients according to the present disclosure fulfil the requirements listed in REGULATION (EU) No. 609/2013."

"Malnutrition" as used herein refers to one or both of Option I: body mass index (BMI, kg/m2)<18.5; Option II: the combined finding of unintentional weight loss (mandatory) and at least one of either reduced BMI or a low fat free mass index (FFMI). Weight loss is defined as either >10% of habitual weight indefinite of time, or >5% over 3 months. Reduced BMI is <20 or <22 kg/m2 in subjects younger and older than 70 years, respectively. Low FFMI is <15 and <17 kg/m2 in females and males, respectively.

The term "(nutritional) therapy" as used herein refers to therapy, preferably nutritional therapy.

A composition "consisting of" a number of ingredients or components is to be understood as comprising no other than the named ingredients or components. In case ranges for amounts of ingredients or components are given, the individual amount of all ingredients or components within the composition has of course also to be adapted such that the sum of all amounts of all present ingredients or components adds up to 100 wt %.

"Homogenization" as used herein refers to the process of diminishing the size of the fat globules in a nutritional emulsion. A preferred homogenization process herein comprises two homogenization steps. The first homogenization step may be carried out at a pressure of 100 bar and the second homogenization step may be carried out at a pressure of 50 bar. Both steps may be carried out at a temperature of 60-80° C., such as 65-75° C., for example 65° C.

"UHT-treatment" aims at killing of microorganisms. Preferred UHT treatment may be carried out with a pre-heat treatment at 90° C. for 3 min followed by UHT at 139° C. for 6 seconds, followed by a (third) homogenization step requiring homogenization at less than 90° C. with a pressure that can oscillate between 40-150 bar.

The term "protein bound amino acid" is known to a person skilled in the art. As a person skilled in the art is aware of, a protein is composed of amino acids. Protein bound amino acids are the amino acids which the protein is composed of. In other words, a protein bound amino acid is an amino acid which is bound in a protein. Accordingly, a free amino acid is not a protein bound amino acid. The term "protein" as used in the term "protein bound amino acid" preferably refers to a protein having an average molecular weight ($M_w$) of ≥500 Da, preferably ≥800 Da, more preferably ≥1000 Da. The term "protein" as used in the term "protein bound amino acid" preferably refers to a protein having an average molecular weight ($M_w$) of ≤100 kDa, preferably ≤80 kDa, more preferably ≤60 kDa. In particularly preferred embodiments, the amino acids are bound in collagen hydrolysate or milk protein. One advantage of the use of protein bound amino acids over free amino acids is the improved taste associated therewith.

"Protein component" as used herein refers to the entirety of ingredients of the nutritional composition declarable as "protein".

"Hydrolysed collagen" or "collagen hydrolysate" as used herein refers to low molecular weight collagen obtainable by hydrolysis of collagen by procedures known to the skilled artisan. Embodiments of hydrolysed collagen as preferred herein have an average molecular weight $M_w$ of from 1000 Da to 6000 Da, preferably 1000 to 3000 Da. Methods for determining the average molecular weight are well known in the art. An exemplary method is given hereinbelow.

"Lipid component" as used herein refers to the entirety of ingredients of the nutritional composition declarable as "fat". The term "PUFA" as used herein refers to polyunsaturated fatty acids. The term "omega-6-PUFA" as used herein refers to omega-6-polyunsaturated fatty acids. The term "omega-3-PUFA" as used herein refers to omega-3-polyunsaturated fatty acids. The term "MUFA" as used herein refers to monounsaturated fatty acids. The term "SFA" as used herein refers to saturated fatty acids.

"Carbohydrate component" as used herein refers to the entirety of ingredients of the nutritional composition declarable as "carbohydrate".

"EN %" refers to the contribution of a certain component or of a specific ingredient to the total nutritional energy of an edible composition, e.g. the nutritional composition.

"Ready-to-use" refers to the final form of the nutritional composition as administered to a patient. Typically, the nutritional compositions herein are pre-packed in a ready to use format, i.e. sold in separately packed dose units that do not require any further dilution etc.

If not specified otherwise, the expression "/100 mL" as used herein means "per 100 mL of the nutritional composition". For example, if not specified otherwise, the expression "g/100 mL" as used herein refers to "g per 100 mL of the nutritional composition", the expression "mg/100 mL" as used herein refers to "mg per 100 mL of the nutritional composition", and the expression "µg/100 mL" as used herein refers to "µg per 100 mL of the nutritional composition", etc.

Nutritional Compositions

The nutritional compositions herein comprise nutrients in predetermined and controllable amounts. A nutritional composition according to the present disclosure comprises a protein component, a lipid component and vitamins. Optionally, such a nutritional composition may further comprise a carbohydrate component. Optionally, such a nutritional composition may further comprise minerals. Optionally, such a nutritional composition may further comprise dietary fibres and/or further ingredients known as food additives. In particularly preferred embodiments, such a nutritional composition further comprises water.

Preferably, the nutritional compositions have a high caloric density. Also preferably, the nutritional compositions have a high protein content. Particularly preferably, the nutritional compositions have a high caloric density and a high protein content.

Typically, the nutritional compositions have a caloric density of at least 2.0 kcal/mL, preferably at least 2.5 kcal/mL, more preferably at least 2.6 kcal/mL, even more preferably at least 2.8 kcal/mL, even more preferably at least 3.0 kcal/mL, even more preferably at least 3.1 kcal/mL. Typically, the nutritional compositions have a caloric density of at most 5.0 kcal/mL, preferably at most 4.0 kcal/mL, more preferably at most 3.8 kcal/mL, even more preferably at most 3.6 kcal/mL, even more preferably at most 3.4 kcal/mL, even more preferably at most 3.3 kcal/mL. Preferably, the nutritional compositions have a caloric density of 2.0-5.0 kcal/mL, preferably 2.5-4.0 kcal/mL, more preferably 2.6-3.8 kcal/mL, even more preferably 2.8-3.6 kcal/mL, even more preferably 3.0-3.4 kcal/mL, even more preferably 3.1-3.3 kcal/mL. Particular preference is also given to nutritional compositions having a caloric density of 3.0-4.0 kcal/mL.

The nutritional compositions herein may comprise a protein component, a lipid component, a carbohydrate component, wherein a. the protein component provides at least 15 EN %, preferably at least 18 EN %, more preferably at least 19 EN % based on the total energy of the nutritional composition;
b. the lipid component provides 40-50 EN % based on the total energy of the nutritional composition;
c. the carbohydrate component provides at least 20 EN % based on the total energy of the nutritional composition.

Preferably, the nutritional compositions according to the present disclosure comprise a protein component, a lipid component, a carbohydrate component, wherein a. the protein component provides 15-25 EN %, preferably 18-22 EN %, more preferably 19-21 EN % based on the total energy of the nutritional composition;
b. the lipid component provides 40-50 EN %, preferably 43-47 EN %, more preferably 44-46 EN % based on the total energy of the nutritional composition; and
c. the carbohydrate component provides 30-40 EN %, preferably 33-37 EN %, more preferably 34-36 EN % based on the total energy of the nutritional composition.

In preferred embodiments, the nutritional compositions herein comprise 40-60 wt %, preferably 45-55 wt % of water based on the total weight of the nutritional composition. In preferred embodiments, the nutritional compositions herein comprise 45-65 vol %, preferably 50-60 vol % of water based on the total volume of the nutritional composition.

The nutritional compositions typically are liquid or semi-solid. In preferred embodiments, the nutritional composition is an emulsion. In particularly preferred embodiments, the nutritional composition is an oil-in-water (O/W) emulsion.

Preferably, the nutritional composition of the present disclosure is nutritionally complete.

Preferably, the nutritional composition of the present disclosure is a ready to use nutritional composition.

The nutritional composition of the present disclosure is administered enterally, preferably orally.

The nutritional composition of the invention shows good tolerability and palatability resulting in excellent compliance. Good compliance is important because it helps to increase a patient's total protein and energy intake.

In preferred embodiments, the nutritional composition herein comprises the following components in the following amounts:

|  | Embodiment I | Embodiment II |
| --- | --- | --- |
| Protein: | 19-21 EN % | 20 EN % |
| Collagen hydrolysate 80% |  | 16 g/100 mL |
| Milk protein 20% |  |  |
| glycine* | 3.2-3.7 g/100 mL | 3.42 g/100 mL |
| arginine* | 0.9-1.2 g/100 mL | 1.05 g/100 mL |
| tryptophan* | 0.04-0.07 g/100 mL | 0.05 g/100 mL |
| proline* | 2.2-2.6 g/100 mL | 2.38 g/100 mL |
| cysteine* | 0.02-0.05 g/100 mL | 0.03 g/100 mL |
| Fat: | 44-46 EN % | 45 EN % |
| Rapeseed oil |  | 16 g/100 mL |
| of which SFA | 2-4 EN % | 3 EN % |
|  |  | 1.1 g/100 mL |
| of which MUFA | 26-30 EN % | 28 EN % |
|  |  | 9.9 g/100 mL |
| of which PUFA | 13-15 EN % | 14 EN % |
|  |  | 5.0 g/100 mL |
| CHO | 34-36 EN % | 35 EN % |
|  |  | 28 g/100 mL |
| Caloric density | 3.1-3.3 kcal/mL, preferably 3.2 kcal/mL | 3.2 kcal/mL |
| Water | 50-60 mL/100 mL | 56 mL/100 mL |
| FSMP balanced** | yes | yes |
| Vitamin D3 | 7.5-8.5 µg/100 mL | 8 µg/100 mL |
| Vitamin E | 5.5-6.0 mg/100 mL (alpha-TE) | 5.67 mg/100 mL (alpha-TE) |

*Bound in collagen hydrolysate or milk protein
**Nutritionally complete in vitamins and minerals In more preferred embodiments, the nutritional composition herein comprises the following components in the following amounts:

|  | Embodiment III | Embodiment IV |
|---|---|---|
| Protein: | 19-21 EN % | 20 EN % |
| Collagen hydrolysate 80% |  | 16 g/100 mL |
| Milk protein 20% |  |  |
| glycine* | 3.2-3.7 g/100 mL | 3.42 g/100 mL |
| arginine* | 0.9-1.2 g/100 mL | 1.05 g/100 mL |
| tryptophan* | 0.04-0.07 g/100 mL | 0.05 g/100 mL |
| proline* | 2.2-2.6 g/100 mL | 2.38 g/100 mL |
| cysteine* | 0.02-0.05 g/100 mL | 0.03 g/100 mL |
| Fat: | 44-46 EN % | 45 EN % |
| Rapeseed oil |  | 16 g/100 mL |
| of which SFA | 2-4 EN % | 3 EN % |
|  |  | 1.1 g/100 mL |
| of which MUFA | 26-30 EN % | 28 EN % |
|  |  | 9.9 g/100 mL |
| of which PUFA | 13-15 EN % | 14 EN % |
|  |  | 5.0 g/100 mL |
| CHO | 34-36 EN % | 35 EN % |
|  |  | 28 g/100 mL |
| Caloric density | 3.1-3.3 kcal/mL, preferably 3.2 kcal/mL | 3.2 kcal/mL |
| Water | 50-60 mL/100 mL | 56 mL/100 mL |
| FSMP balanced** | yes | yes |
| Calcium | 150-175 mg/100 mL | 160 mg/100 mL |
| Zinc | 3.0-4.0 mg/100 mL | 3.5 mg/100 mL |
| Copper | 480-540 µg/100 mL | 512 µg/100 mL |
| Selenium | 20-25 µg/100 mL | 23 µg/100 mL |
| Vitamin D3 | 7.5-8.5 µg/100 mL | 8 µg/100 mL |
| Vitamin E | 5.5-6.0 mg/100 mL (alpha-TE) | 5.67 mg/100 mL (alpha-TE) |
| Vitamin B6 | 0.55-0.62 mg/100 mL | 0.58 mg/100 mL |
| Vitamin B12 | 1.0-1.2 µg/100 mL | 1.1 µg/100 mL |
| Folic acid | 60-75 µg/100 mL | 67.2 µg/100 mL |
| Vitamin C | 35-50 mg/100 mL | 41.6 mg/100 mL |

*Bound in collagen hydrolysate or milk protein
**Nutritionally complete in vitamins and minerals In even more preferred embodiments, the nutritional composition herein comprises the following components in the following amounts:

|  | Embodiment V | Embodiment VI |
|---|---|---|
| Protein: | 19-21 EN % | 20 EN % |
| Collagen hydrolysate 80% |  | 16 g/100 mL |
| Milk protein 20% |  |  |
| glycine* | 3.2-3.7 g/100 mL | 3.42 g/100 mL |
| arginine* | 0.9-1.2 g/100 mL | 1.05 g/100 mL |
| tryptophan* | 0.04-0.07 g/100 mL | 0.05 g/100 mL |
| proline* | 2.2-2.6 g/100 mL | 2.38 g/100 mL |
| cysteine* | 0.02-0.05 g/100 mL | 0.03 g/100 mL |
| Fat: | 44-46 EN % | 45 EN % |
| Rapeseed oil |  | 16 g/100 mL |
| of which SFA | 2-4 EN % | 3 EN % |
|  |  | 1.1 g/100 mL |
| of which MUFA | 26-30 EN % | 28 EN % |
|  |  | 9.9 g/100 mL |
| of which PUFA | 13-15 EN % | 14 EN % |
|  |  | 5.0 g/100 mL |
| CHO | 34-36 EN % | 35 EN % |
|  |  | 28 g/100 mL |
| Caloric density | 3.1-3.3 kcal/mL, preferably 3.2 kcal/mL | 3.2 kcal/mL |
| Water | 50-60 mL/100 mL | 56 mL/100 mL |
| FSMP balanced** | yes | yes |
| Sodium | 100-125 mg/100 mL | 112 mg/100 mL |
| Potassium | 290-340 mg/100 mL | 312 mg/100 mL |
| Chloride | 130-160 mg/100 mL | 144 mg/100 mL |
| Calcium | 150-175 mg/100 mL | 160 mg/100 mL |
| Magnesium | 35-45 mg/100 mL | 40 mg/100 mL |
| Phosphorus | 100-125 mg/100 mL | 112 mg/100 mL |
| Iron | 4.3-5.2 mg/100 mL | 4.8 mg/100 mL |
| Zinc | 3.0-4.0 mg/100 mL | 3.5 mg/100 mL |
| Copper | 480-540 µg/100 mL | 512 µg/100 mL |
| Manganese | 0.9-1.5 mg/100 mL | 1.2 mg/100 mL |
| Iodide | 40-50 µg/100 mL | 44.8 µg/100 mL |
| Fluoride | 0.35-0.45 mg/100 mL | 0.4 mg/100 mL |
| Chromium | 20-25 µg/100 mL | 23 µg/100 mL |
| Molybdenum | 27-35 µg/100 mL | 30.4 µg/100 mL |
| Selenium | 20-25 µg/100 mL | 23 µg/100 mL |
| Vitamin A | 200-250 µg/100 mL (RE***) | 224 µg/100 mL (RE***) |
| Beta-Carotene | 400-450 µg/100 mL | 426 µg/100 mL |
| Vitamin D3 | 7.5-8.5 µg/100 mL | 8 µg/100 mL |
| Vitamin E | 5.5-6.0 mg/100 mL (alpha-TE) | 5.67 mg/100 mL (alpha-TE) |
| Vitamin K1 | 17-25 µg/100 mL | 20.8 µg/100 mL |
| Vitamin B1 | 0.45-0.55 mg/100 mL | 0.5 mg/100 mL |
| Vitamin B2 | 0.47-0.55 mg/100 mL | 0.51 mg/100 mL |
| Niacin | 5.0-5.8 mg/100 mL | 5.4 mg/100 mL |
| Vitamin B6 | 0.55-0.62 mg/100 mL | 0.58 mg/100 mL |
| Vitamin B12 | 1.0-1.2 µg/100 mL | 1.1 µg/100 mL |
| Pantothenic acid | 1.80-2.10 mg/100 mL | 1.92 mg/100 mL |
| Biotin | 13.0-16.0 µg/100 mL | 14.4 µg/100 mL |
| Folic acid | 60-75 µg/100 mL | 67.2 µg/100 mL |
| Vitamin C | 35-50 mg/100 mL | 41.6 mg/100 mL |

*Bound in collagen hydrolysate or milk protein
**Nutritionally complete in vitamins and minerals
***Retinol equivalents Protein Component The invention involves the use of the protein bound amino acids glycine, arginine and tryptophan. Accordingly, the nutritional composition herein comprises a protein component.

According to the invention, the nutritional composition comprises 2.5-4.5 g/100 mL glycine. Typically, the nutritional composition comprises 3.0-4.0 g/100 mL glycine, preferably 3.2-3.7 g/100 mL glycine. Preferably, at least 80 mol %, more preferably at least 90 mol %, even more preferably at least 95 mol %, even more preferably at least 98 mol %, most preferably at least 99 mol % of the glycine comprised in the nutritional composition is protein bound. Glycine promotes the synthesis of creatine in the body, which helps to build lean muscle mass and raise energy levels in the muscles by synthesizing muscle protein increasing nitrogen retention.

According to the invention, the nutritional composition comprises 0.5-1.5 g/100 mL arginine. Typically, the nutritional composition comprises 0.8-1.3 g/100 mL arginine, preferably 0.9-1.2 g/100 mL arginine. Preferably, at least 80 mol %, more preferably at least 90 mol %, even more preferably at least 95 mol %, even more preferably at least 98 mol %, most preferably at least 99 mol % of the arginine comprised in the nutritional composition is protein bound. Arginine promotes creatine synthesis in the body, which supports muscle metabolism by maintaining a healthy nitrogen balance, which helps to increase muscle mass.

According to the invention, the nutritional composition comprises at least 0.02 g/100 mL tryptophan. Typically, the nutritional composition comprises 0.02-0.2 g/100 mL tryptophan, preferably 0.03-0.1 g/100 mL tryptophan, more preferably 0.04-0.07 g/100 mL tryptophan. Preferably, at least 80 mol %, more preferably at least 90 mol %, even more preferably at least 95 mol %, even more preferably at least 98 mol %, most preferably at least 99 mol % of the tryptophan comprised in the nutritional composition is protein bound. Tryptophan is an indispensable amino acid, which helps to ensure normal protein metabolism.

Optionally, the nutritional composition further comprises proline, preferably 1.5-4.0 g/100 mL proline, more preferably 2.0-3.0 g/100 mL proline, even more preferably 2.2-2.6 g/100 mL proline. Preferably, at least 80 mol %, more preferably at least 90 mol %, even more preferably at least 95 mol %, even more preferably at least 98 mol %, most preferably at least 99 mol % of the proline optionally comprised in the nutritional composition is protein bound.

Optionally, the nutritional composition further comprises cysteine, preferably at least 0.01 g/100 mL cysteine, more preferably 0.01-0.1 g/100 mL cysteine, even more preferably 0.02-0.05 g/100 mL cysteine. Preferably, at least 80 mol %, more preferably at least 90 mol %, even more preferably at least 95 mol %, even more preferably at least 98 mol %, most preferably at least 99 mol % of the cysteine optionally comprised in the nutritional composition is protein bound.

In preferred embodiments, the protein component comprises collagen or hydrolysed collagen. In particularly preferred embodiments, the protein component comprises hydrolysed collagen. In other preferred embodiments, the protein component comprises collagen. In other preferred embodiments, the protein component comprises collagen and hydrolysed collagen.

In preferred embodiments, the protein component comprises a protein source selected from vegetable proteins, animal proteins other than collagen and mixtures thereof, for example milk protein, soy protein, pea protein, egg white and hydrolysates thereof. In preferred embodiments, the protein component comprises a protein source selected from milk proteins, such as total milk protein, milk protein isolate, milk protein concentrate, whey, casein and mixtures thereof.

In preferred embodiments, the protein component comprises collagen or collagen hydrolysate as (a) protein source(s) and milk protein as a protein source. In particularly preferred embodiments, the protein component comprises collagen hydrolysate as a first protein source and milk protein as a second protein source. In other preferred embodiments, the protein component comprises collagen as a first protein source and milk protein as a second protein source. In other preferred embodiments, the protein component comprises collagen, collagen hydrolysate and milk protein as protein sources.

Preferably, the protein component comprises at least two different protein sources. More preferably, the protein component comprises at least two different protein sources, wherein the first protein source is hydrolysed collagen. In even more preferred embodiments, the protein component comprises at least two different protein sources, wherein the first protein source is hydrolysed collagen and represents at least 35 wt %, preferably 45-95 wt %, more preferably 55-90 wt %, even more preferably 70-90 wt %, most preferably 80-85 wt % based on the total weight of the protein component.

In particularly preferred embodiments, the protein component essentially consists of collagen hydrolysate and milk protein. In particularly preferred embodiments, the protein component consists of collagen hydrolysate and milk protein.

Comparing nutritional compositions comprising high amounts of hydrolysed protein, the nutritional compositions comprising hydrolysed collagen (which are according to preferred embodiments of the invention) should lead to improved patient compliance due to improved rheological and sensorial properties like viscosity, texture and/or taste.

In preferred embodiments, the second protein source is selected from vegetable proteins, animal proteins other than collagen and mixtures thereof, for example milk protein, soy protein, pea protein, egg white and hydrolysates thereof. In more preferred embodiments, the second protein source is selected from milk proteins, such as total milk protein, milk protein isolate, milk protein concentrate, whey, casein and mixtures thereof. A particularly preferred second protein source is milk protein, e.g. total milk protein and/or milk protein concentrate.

Within the second protein source, proteins having different average molecular weights may be used. Preferred average molecular weights ($M_w$) of the proteins used within the second protein source lie in the range of 20-60 kDa. In such a range properties of the nutritional composition can be well balanced in terms of heat stability and/or viscosity.

For example, a second protein source comprising a high amount of a protein having a lower molecular weight will lead to a reduced viscosity of the nutritional composition. Therefore, a preferred second protein source comprises more than 40 wt %, preferably more than 50 wt % of a protein having an average molecular weight of less than 40 kDa, such as 20-40 kDa (based on the total weight of the second protein source).

A preferred protein component comprises collagen hydrolysate as the first protein source and milk protein as the second protein source. Such a protein component is particularly suitable as it can be adapted such that it provides an amino acid distribution suitable to meet current international recommendations for daily intake (e.g. when the nutritional compositions of the present disclosure are used as sole source of nutrition), even without addition of free amino acids, di- or tripeptides. Such an exemplary international recommendation has been published by the WHO (Technical Report Series 935, 2007, p. 150). Particularly preferred is a protein component comprising 70-90 wt % of hydrolysed collagen as the first protein source and 30-10 wt % milk protein as the second protein source, such as 80 wt % hydrolysed collagen with 20 wt % milk protein (each based on the total weight of the protein component).

Further amino acids may as well contribute to the protein component, preferably the second protein source. These may be added in their chemical form or in the form of low molecular peptides, such as di- or tripeptides. However, in preferred embodiments neither free amino acids nor di- or tripeptides are added to the protein component described herein.

Nutritional compositions herein typically comprise at least 10 wt %, preferably at least 12 wt %, more preferably at least 13 wt % of protein based on the total weight of the nutritional composition.

Nutritional compositions herein typically comprise at least 14 g, preferably at least 15 g, more preferably at least 15.5 g, most preferably at least 16 g of protein per 100 mL of the nutritional composition. Nutritional compositions herein typically comprise at most 20 g, preferably at most 18 g, more preferably at most 17.0 g of protein per 100 mL of the nutritional composition. Preferably, nutritional compositions herein comprise 14-20 g, more preferably 15-18 g, most preferably 15.5-17.0 g of protein per 100 mL of the nutritional composition.

In preferred embodiments, the protein component provides at least 15 EN %, preferably at least 18 EN %, more preferably at least 19 EN % based on the total energy of the nutritional composition. For example, the protein component provides 15-25 EN %, preferably 18-22 EN %, more preferably 19-21 EN % based on the total energy of the nutritional composition.

Preferably, the protein to water ratio of the present nutritional composition is at least 2.0/10 [g/g], more preferably at least 2.5/10 [g/g].

As described above, the collagen hydrolysate, which is used in preferred embodiments of the invention, preferably has an average molecular weight $M_w$ of from 1000 Da to 6000 Da, more preferably 1000 to 3000 Da. Examples are known to a person skilled in the art and commercially available (e.g. via Gelita, Germany). Such hydrolysates and methods for making them are for example described in DE 102010060564 A1, in particular par. [0004]-[0011] and Example 1 with the low molecular weight hydrolysates in par. [0030] being particularly suitable. Of course, other sources than porcine gelatin can be used, with bovine being particularly preferred for the applications herein.

Accordingly, particularly preferred collagen hydrolysates have molecular weight distributions as listed below:

| Mol. weight range | Upper limit |
|---|---|
| >7500 Da | 10 wt % |
| >3500-7500 Da | 35 wt % |
| >1500-3500 Da | 35 wt % |
| >500-1500 Da | 50 wt % |
| <500 Da | 15 wt % |

| Mol. weight range | Preferred range | Particularly preferred range | Example A | Example B |
|---|---|---|---|---|
| >7500 Da | ≤10 wt % | ≤5 wt % | ≤5 wt % | ≤5 wt % |
| >3500-7500 Da | 10-35 wt % | 10-20 wt % | 10-20 wt % | 12-18 wt % |
| >1500-3500 Da | 20-35 wt % | 25-32 wt % | 25-32 wt % | 25-31 wt % |
| >500-1500 Da | 30-50 wt % | 40-50 wt % | 40-50 wt % | 40-46 wt % |
| <500 Da | ≤15 wt % | ≤15 wt % | ≤15 wt % | 5-10 wt % |

Preferably, at most 10 wt %, more preferably at most 5 wt % of the collagen hydrolysate has a molecular weight of above 7,500 Da.

Preferably, at most 15 wt %, more preferably at most 5 wt % of the collagen hydrolysate has a molecular weight of below 500 Da.

Thus, particularly preferred collagen hydrolysates are characterized by at least 75 wt %, preferably at least 90 wt % falling into the molecular weight range of 500-7500 Da.

Lipid Component

The nutritional composition herein comprises a lipid component. Said lipid component may comprise one or more lipid sources, such as lipids of animal and/or vegetable origin. Suitable lipid sources may be selected from oil of marine origin vegetable oils and combinations thereof. Preferably, lipid sources may be selected from fish oil, sunflower oil, safflower oil, soy oil, rapeseed oil, canola oil, linseed oil and combinations thereof. Additionally, the lipid component may comprise MCT in oil or fat form providing C6-C12 fatty acids.

In preferred embodiments, the lipid component comprises rapeseed oil and/or canola oil, preferably rapeseed oil, also preferably canola oil.

In terms of individual fatty acids, the lipid component typically includes polyunsaturated fatty acids, monounsaturated fatty acids and saturated fatty acids. Suitable fatty acids may be selected from the group consisting of caproic acid (C6:0), caprylic acid (C8:0), capric acid (C10:0), lauric acid (C12:0), myristic acid (C14:0), palmitic acid (C16:0), palmitoleic acid (C16:1ω7), stearic acid (C18:0), oleic acid (C18:1ω9), linoleic acid (C18:2ω6), a-linolenic acid (C18:3ω3), eicosapentaenoic acid (C20:5ω3), docosahexaenoic acid (C22:6ω3) and mixtures thereof. Particularly preferred fatty acids are linoleic acid, alpha-linolenic acid and mixtures thereof.

Fat is a rich source of energy which is invaluable when meeting a patient's nutritional requirements especially in a small volume. It supports the absorption of fat-soluble vitamins, such as vitamins D and E.

In the nutritional composition of the invention, the percentage energy from fat is higher than the current global nutrition society recommendations for an optimal fat supply in the healthy population. Such higher percentage energy from fat is, however, not contraindicated in the malnourished population. In populations with inadequate total energy intake, dietary fats are an important macronutrient to increase energy intake to appropriate levels. The fat content in the present nutritional composition is appropriate for the malnourished population.

PUFA are a concentrated source of energy and have many benefits. For example, replacing SFA by PUFA reduces the risk of coronary heart disease (CHD). The risk of metabolic syndrome components and diabetes can be reduced as well.

In the nutritional composition of the invention, the percentage energy from PUFA is higher than the WHO recommendation. This recommendation is related to low tocopherol (vitamin E) intake. The main risk in a higher total PUFA dietary intake is thought to be an increased risk of lipid peroxidation. The present nutritional composition provides vitamin E in sufficient amounts, which will not only help the patients to meet their vitamin E requirements but may also further reduce the impact or risk of lipid peroxidation. The PUFA content in the present nutritional composition is appropriate for the malnourished population due to the need for a positive energy balance to promote weight gain in a small volume.

According to the invention, the lipid component provides 40-50 EN % based on the total energy of the nutritional composition. Preferably, the lipid component provides 43-47 EN %, more preferably 44-46 EN % based on the total energy of the nutritional composition.

According to the invention, 12-16 EN % based on the total energy of the nutritional composition is provided by PUFA. Preferably, 13-15 EN % based on the total energy of the nutritional composition is provided by PUFA.

In preferred embodiments, 8-12 EN %, preferably 8.5-10.5 EN % based on the total energy of the nutritional composition is provided by omega-6-PUFA. An example of an omega-6-PUFA is linoleic acid. In preferred embodiments, 3-5 EN %, preferably 3.5-5.0 EN % based on the total energy of the nutritional composition is provided by omega-3-PUFA. An example of an omega-3-PUFA is alpha-linolenic acid. Preferably, the ratio [g/g] of omega-6-PUFA to omega-3-PUFA is 1.6-4.0, more preferably 1.7-3.0.

In preferred embodiments, 24-32 EN %, preferably 26-30 EN %, for example 28 EN %, based on the total energy of the nutritional composition is provided by MUFA. In preferred embodiments, 1-5 EN %, preferably 2-4 EN %, for example 3 EN %, based on the total energy of the nutritional composition is provided by SFA.

Carbohydrate Component

The nutritional composition herein may comprise a carbohydrate component. Said carbohydrate component may comprise one or more carbohydrate sources. Typical carbohydrate sources may be selected from the group consisting of maltodextrine, glucose syrup, sucrose, fructose, isomaltulose, starch (modified or unmodified), tapioca dextrine, and mixtures thereof.

Typically, the carbohydrate component provides at least 20 EN %, preferably 30-40 EN %, more preferably 33-37 EN %, for example 34-36 EN % based on the total energy of the nutritional composition.

A preferred carbohydrate component comprises glucose syrup and, preferably sucrose. The carbohydrate component may comprise 65-95 wt % of glucose syrup and 5-35 wt % of sucrose based on the total weight of the carbohydrate component. Preferably, the carbohydrate component comprises 60-80 wt % glucose syrup and 20-40 wt % sucrose, for example 65-75 wt % glucose syrup and 25-35 wt % sucrose based on the total weight of the carbohydrate component.

Vitamins and Minerals

To be regarded as nutritionally complete, nutritional compositions have to comprise vitamins and minerals.

Suitable vitamins to be included in the composition in order to render it nutritionally complete according to the present disclosure are Vitamin A, Vitamin D, Vitamin K, Vitamin C, Thiamin, Riboflavin, Vitamin B6, Niacin, Folic acid, Vitamin B12, Pantothenic acid, Biotin and Vitamin E. An example for rendering a nutritional composition complete in vitamins is given in table 2.

Suitable minerals to be included in the composition in order to render it nutritionally complete according to the present disclosure are Sodium, Chloride, Potassium, Calcium, Phosphorus, Magnesium, Iron, Zinc, Copper, Iodine, Selenium, Manganese, Chromium and Molybdenum. Optionally, Fluoride may be included. An example for rendering a nutritional composition complete in minerals is given in table 3.

According to the invention, the nutritional composition comprises 4.0-8.0 mg/100 mL alpha-TE vitamin E. Typically, the nutritional composition comprises 4.5-7.0 mg/100 mL alpha-TE vitamin E, preferably 5.0-6.5 mg/100 mL alpha-TE vitamin E, more preferably 5.2-6.2 mg/100 mL alpha-TE vitamin E, even more preferably 5.5-6.0 mg/100 mL alpha-TE vitamin E. The term "alpha-TE" used in connection with vitamin E refers to alpha-tocopherol equivalents. Vitamin E helps to further reduce the impact or risk of lipid peroxidation. Furthermore, vitamin E has antioxidant properties and, thus, may protect tissue from oxidative damage.

According to the invention, the nutritional composition comprises 5.0-12.0 µg/100 mL vitamin D. Typically, the nutritional composition comprises 6.0-10.5 µg/100 mL vitamin D, preferably 7.0-9.5 µg/100 mL vitamin D, more preferably 7.2-9.0 µg/100 mL vitamin D, even more preferably 7.5-8.5 µg/100 mL vitamin D. The term "vitamin D" as used herein preferably refers to vitamin D3. Vitamin D modulates intestinal calcium absorption and calcium release from bone, as well as renal phosphate excretion in order to maintain plasma calcium and phosphate concentrations in a range supporting cellular processes, neuromuscular function, and bone ossification. Above its role in bone metabolism, vitamin D has additional extra-skeletal influences on the cardiovascular system, the endocrine system, the immune system and the nervous system. Benefits associated with adequate vitamin D levels include improvements in bone health and skeletal muscle function, prevention or reduced risk of falls, fractures and osteoporosis as well as lower mortality. An adequate intake of vitamin D in conjunction with high protein intake helps to increase muscle mass.

Optionally, the nutritional composition further comprises B vitamins, preferably at least 5 mg/100 mL B vitamins, more preferably 6-20 mg/100 mL B vitamins, even more preferably 7-12 mg/100 mL B vitamins. Examples of B vitamins are vitamin B1, vitamin B2, niacin, vitamin B6, vitamin B12, pantothenic acid, biotin and folic acid. In preferred embodiments, the nutritional composition comprises vitamin B6, vitamin B12 and folic acid. In particularly preferred embodiments, the nutritional composition comprises vitamin B1, vitamin B2, niacin, vitamin B6, vitamin B12, pantothenic acid, biotin and folic acid. B vitamins, in particular vitamin B6, vitamin B12 and folic acid, help to improve cognitive/psychological function and to decrease cardiovascular risk.

Optionally, the nutritional composition further comprises vitamin B6, preferably 0.3-1.0 mg/100 mL vitamin B6, more preferably 0.5-0.7 mg/100 mL vitamin B6, even more preferably 0.55-0.62 mg/100 mL vitamin B6. Optionally, the nutritional composition further comprises vitamin B12, preferably 0.6-2.0 µg/100 mL vitamin B12, more preferably 0.8-1.5 µg/100 mL vitamin B12, even more preferably 1.0-1.2 µg/100 mL vitamin B12. Optionally, the nutritional composition further comprises folic acid, preferably 40-100 µg/100 mL folic acid, more preferably 50-85 µg/100 mL folic acid, even more preferably 60-75 µg/100 mL folic acid.

Optionally, the nutritional composition further comprises vitamin C, preferably 20-80 mg/100 mL vitamin C, more preferably 30-60 mg/100 mL vitamin C, even more preferably 35-50 mg/100 mL vitamin C.

Optionally, the nutritional composition further comprises calcium, preferably 50-300 mg/100 mL calcium, more preferably 120-200 mg/100 mL calcium, even more preferably 150-175 mg/100 mL calcium. Calcium, in particular in combination with vitamin D, helps to improve bone health and to reduce the risk of bone fragility, osteoporosis and bone fracture.

Optionally, the nutritional composition further comprises zinc, preferably 2.0-5.0 mg/100 mL zinc, more preferably 2.5-4.5 mg/100 mL zinc, even more preferably 3.0-4.0 mg/100 mL zinc.

Optionally, the nutritional composition further comprises copper, preferably 400-600 µg/100 mL copper, more preferably 450-570 µg/100 mL copper, even more preferably 480-540 µg/100 mL copper.

Optionally, the nutritional composition further comprises selenium, preferably 10-40 µg/100 mL selenium, more preferably 15-30 µg/100 mL selenium, even more preferably 20-25 µg/100 mL selenium.

In one embodiment, the nutritional composition further comprises vitamin B6, vitamin B12, folic acid, copper and selenium, preferably in the amounts specified above.

In one embodiment, the nutritional composition further comprises vitamin C and zinc, preferably in the amounts specified above.

Fibre

The nutritional composition herein may comprise ingredients declarable as dietary fibres. Suitable dietary fibres may be selected from the group consisting of cocoa powder, inulin, wheat dextrine, cellulose, microcrystalline cellulose, soy polysaccharides, tapioca dextrine, xanthan, fructooligosaccharides, galactooligosaccharides, at least partially hydrolysed guar gum, acacia gum, pectin, oat fibre, polydextrose, resistant starch, hemicellulose and mixtures thereof.

Additives

Nutritional compositions optionally comprise food additives. Additives are typically present in total amount of less than 10 wt %, 5 wt % or even less than 1 wt % based on the total weight of the nutritional composition. Exemplary additives are choline, beta-carotene, lutein, lycopene, caffeine, lecithin, taurine, carnitine, myo-inositol, colorants, aroma and mixtures thereof. Aromas may be caramel, vanilla, yoghurt, chocolate, coffee, cappuccino, fruit aromas and the like.

The additives may include stabilisers and emulsifiers. Preferably, the stabilisers are selected from gums and mixtures thereof. For example, microcrystalline cellulose (E460), sodium carboxymethylcellulose (E466), carrageenan (E407), diacetyl tartaric acid ester of glycerides, cellulose gel (cellulose, microcrystalline) can be used. The emulsifiers may be selected from (destilled) monoglycerides such as E471, soy lecithins. For example, stabilizers and emulsifiers are included in the following amounts/ratios monoglycerides (E471, as an emulsifier) 1-5 g/L and a stabilizer mixture comprising 0.3-5 g/L, soy lecithin 1-5 g/L, diacetyl tartaric acid of glycerides (E472, eg. DATEM) 0.1-5 g/L and MCC 1-8 g/L.

Use in Therapy

According to the invention, the nutritional composition is used in therapy of patients with sarcopenia and/or frailty or pre-sarcopenic and/or pre-frail patients. In one embodiment, the nutritional composition is used in therapy of patients with sarcopenia and/or frailty. In another embodiment, the nutritional composition is used in therapy of pre-sarcopenic and/or pre-frail patients. In preferred embodiments, therapy refers to nutritional therapy. In preferred embodiments, the nutritional composition is used as patient nutrition.

In the context of the present invention, the patients are elderly patients. Elderly patients are patients at or after the age of 65 (age ≥65), preferably at or after the age of 70 (age ≥70), more preferably at or after the age of 75 (age ≥75). The patients can, for example, be at home or in a nursing home or a hospital.

Preferred patients may have a low body mass index (BMI). Also preferred patients may have a low fat free mass index (FFMI). Particularly preferred patients may have a low body mass index (BMI) and a low fat free mass index (FFMI).

Preferred patients are elderly patients (age≥65) having a BMI of <22 kg/m2, preferably <20 kg/m2, more preferably <18.5 kg/m2, even more preferably <17 kg/m2, even more preferably <16 kg/m2.

Also preferred patients are elderly patients (age≥65) having an FFMI of <16 kg/m2, preferably <15 kg/m2, more preferably <14 kg/m2, even more preferably <13 kg/m2, if they are female, and having an FFMI of <18 kg/m2, preferably <17 kg/m2, more preferably <16 kg/m2, even more preferably <15 kg/m2, if they are male.

Particularly preferred patients are elderly patients (age≥65) having a BMI of <22 kg/m2, preferably <20 kg/m2, more preferably <18.5 kg/m2, even more preferably <17 kg/m2 even more preferably <16 kg/m2 and having an FFMI of <16 kg/m2, preferably <15 kg/m2, more preferably <14 kg/m2, even more preferably <13 kg/m2, if they are female, and having an FFMI of <18 kg/m2, preferably <17 kg/m2, more preferably <16 kg/m2, even more preferably <15 kg/m2, if they are male.

In one preferred embodiment, the nutritional composition is used in the prevention or treatment of malnutrition, preferably protein malnutrition, also preferably protein-energy malnutrition (PEM).

In one preferred embodiment, the nutritional composition is used in the prevention or treatment of nutrient deficiencies associated with malnutrition, preferably protein malnutrition, also preferably protein-energy malnutrition (PEM).

In one preferred embodiment, the nutritional composition is used in therapy of patients with sarcopenia or pre-sarcopenic patients.

Generally, patients with sarcopenia suffer from muscle loss. Preferred patients with sarcopenia are patients suffering from the loss of muscle mass and function. Preferred patients with sarcopenia are patients suffering from the loss of muscle mass and strength. Preferred patients with sarcopenia are patients suffering from the loss of muscle mass, muscle function and muscle strength.

Preferred patients with sarcopenia may have a low grip strength. For example, preferred female patients with sarcopenia may have a grip strength of at most 30 kg, preferably at most 24 kg, more preferably at most 18 kg, even more preferably at most 16 kg. For example, preferred male patients with sarcopenia may have a grip strength of at most 40 kg, preferably at most 35 kg, more preferably at most 30 kg, even more preferably at most 26 kg.

Preferred patients with sarcopenia may have a low gait speed. For example, preferred patients with sarcopenia may have a gait speed of <0.8 m/s.

In another preferred embodiment, the nutritional composition is used in therapy of patients with frailty or pre-frail patients.

Preferred patients with frailty are patients which show at least three, preferably at least four, more preferably all of the symptoms selected from the group consisting of weight loss with or without sarcopenia, exhaustion, weakness, slowness and reduced physical activity. More preferred patients with frailty are patients which show the symptom weight loss with or without sarcopenia and at least two, preferably at least three, more preferably all of the symptoms selected from the group consisting of exhaustion, weakness, slowness and reduced physical activity.

Preferred pre-frail patients are patients which show one or two, preferably one, also preferably two of the symptoms selected from the group consisting of weight loss with or without sarcopenia, exhaustion, weakness, slowness and reduced physical activity. More preferred pre-frail patients are patients which show the symptom weight loss with or without sarcopenia and preferably one of the symptoms selected from the group consisting of exhaustion, weakness, slowness and reduced physical activity.

In a particular embodiment, the nutritional composition is used in therapy of patients with sarcopenia and frailty or pre-sarcopenic and pre-frail patients (preferably patients with sarcopenia and frailty).

In another embodiment, the nutritional composition is used in (nutritional) therapy of patients with sarcopenia or pre-sarcopenic patients (preferably patients with sarcopenia), wherein the patients also suffer from cancer.

In another embodiment, the nutritional composition is used in (nutritional) therapy of patients with sarcopenia or pre-sarcopenic patients (preferably patients with sarcopenia), wherein the patients also suffer from Parkinson's disease (PD).

In another embodiment, the nutritional composition is used in (nutritional) therapy of patients with sarcopenia and/or frailty or pre-sarcopenic and/or pre-frail patients (preferably patients with sarcopenia and/or frailty), wherein the patients also suffer from dementia.

In another embodiment, the nutritional composition is used in (nutritional) therapy of patients with sarcopenia or pre-sarcopenic patients (preferably patients with sarcopenia), wherein the patients also suffer from dementia.

In another embodiment, the nutritional composition is used in (nutritional) therapy of patients with frailty or pre-frail patients (preferably patients with frailty), wherein the patients also suffer from dementia.

In another embodiment, the nutritional composition is used in (nutritional) therapy of patients with frailty or pre-frail patients (preferably patients with frailty), wherein the patients also suffer from chronic obstructive pulmonary disease (COPD).

Preferably, the nutritional composition to be administered is provided in a dose unit of 100-200 mL, more preferably 100-150 mL. Also preferably, the nutritional composition to be administered is provided in a dose unit providing 300-500 kcal, more preferably 350-450 kcal. Also preferably, the nutritional composition to be administered is provided in a dose unit providing 15-30 g, more preferably 18-22 g of protein. Particularly preferably, the nutritional composition to be administered is provided in a dose unit of 125 mL providing 400 kcal and 20 g of protein.

Preferably, the nutritional composition is administered in 3-8 dose units daily, preferably 5 dose units daily, for example 5 dose units daily each providing 350-450 kcal, or for example 5 dose units daily each providing 18-22 g of protein. Also preferably, the nutritional composition is administered in 1-3 dose units daily, preferably 1 or 2 dose units daily, for example 1 or 2 dose units daily each providing 350-450 kcal, or for example 1 or 2 dose units daily each providing 18-22 g of protein.

In preferred embodiments, the nutritional composition is administered in a daily dose of 1500-2500 kcal or in a daily dose of 75-125 g of protein. Such daily doses are particularly suitable for complete nutrition. In other preferred embodiments, the nutritional composition is administered in a daily dose of 300-900 kcal or in a daily dose of 15-45 g of protein. Such daily doses are particularly suitable for supplemental nutrition.

To demonstrate the efficacy of a combination of PUFA, vitamin E, vitamin D and the amino acids glycine, arginine and tryptophan, an in vitro study can be conducted. For example, the ability of this combination to rescue the atrophy induced by tumor necrosis factor-alpha (TNF-alpha) as well as its ability to increase protein synthesis can be investigated. TNF-alpha levels increase with age, and increased TNF-alpha levels are connected to muscle atrophy and sarcopenia, see e.g. FASEB J. 2005, 19(6), 668-670 (Phillips et al.). Suitable cells are, for example, human primary myoblasts. Linoleic acid (n-6 PUFA) and/or alpha-linolenic acid (n-3 PUFA) can, for example, be used as PUFA in the in vitro study. Possible readouts include, for example, myotube differentiation and size (width and area), protein synthesis, and/or fusion index. Further possible readouts include, for example, neuromuscular junction (acetylcholine receptor expression) and/or functionality of acetylcholine receptor measured by intracellular $Ca^{++}$ rising after acetylcholine treatment.

Furthermore, the efficacy of the nutritional composition of the invention can, for example be demonstrated using an animal model. Suitable animal models include, among others, mouse models or rat models. For example, aged animals or immobilized animals can be used. Possible readouts include, among others, grip strength and/or muscle force. An in vivo study on sarcopenia, which involves the use of aged rats, is described in, e.g., Exp. Gerontol. 2017, 98, 177-183 (Liao et al.).

To further demonstrate the efficacy of the nutritional composition of the invention, a study in humans can be conducted. For example, its efficacy on muscle protein synthesis can be investigated using a unilateral leg exercise model. Such a study involves unilateral leg exercise and bilateral muscle biopsies before and after exercise. The nutritional composition of the invention can be ingested orally, for example shortly after exercise. Muscle protein synthesis can be quantified using $^{13}C_6$ phenylalanine labeling. $^{13}C_6$ phenylalanine can be added to the nutritional composition of the invention, for example shortly before ingestion.

Preparation of Nutritional Compositions

The nutritional composition can be prepared according to methods known in the art. For example, the nutritional composition can be prepared by mixing and homogenization. The components of the nutritional composition can, for example, be mixed at elevated temperatures, for example at a temperature of 50-90° C. Homogenization can, for example, be carried out at a temperature of <90° C., preferably 60-65° C., and/or at a pressure of 40-200 bar, preferably 40-110 bar, more preferably 50-100 bar. Homogenization can, for example, involve two steps (e.g., a first step which can be carried out at 90-110 bar, for example 100 bar, and a second step which can be carried out at 40-60 bar, for example 50 bar). The nutritional composition can also be sterilized. Sterilization can, for example, involve a pre-heating step (which can, e.g., be carried out at 70-100° C., preferably 85-95° C., e.g. for 2-5 minutes), a heating step (which can, e.g., be carried out at 130-145° C., preferably 139-141° C., e.g. for 6-15 seconds) and an additional homogenization step (which can, e.g., be carried out at a pressure of 40-200 bar, e.g. at <90° C.).

In a preferred embodiment, the nutritional composition can, for example, be prepared by a process which comprises the following steps:
i. a first step, wherein water is provided and heated to a temperature of 50-70° C.;
ii. a second step wherein, optionally, a carbohydrate component—or a fraction thereof—and, optionally, a stabilizer, such as MCC, is added;
iii. a third step, wherein the protein component is added;
iv. a fourth step, wherein the lipid component is added, preferably at an elevated temperature of 80-90° C., preferably in combination with a (further) emulsifier and/or stabilizer, such as soy lecithin and/or diacetyl tartaric acid glycerides (e.g. DATEM), and/or (distilled) monoglycerides;
v. a fifth step, wherein vitamins and, optionally, minerals and, optionally, the remaining fraction of the carbohydrate component and, optionally, any other powder ingredient, e.g. fibres, aroma, and other additives, are added; at any time before, during or after the fifth step, the mixture is allowed to cool to 55-65° C.;
vi. a sixth step, wherein the pH of the mixture is adjusted to 6-9, preferably 7-8, e.g. 7;
vii. a seventh step, wherein the mixture is homogenized, e.g. at 60-65° C. at a pressure of 100/50 bar;
viii. an eighth step, wherein the mixture is sterilized; the eighth step may comprise (8.a) a pre-heating step, (8.b) a heating step and (8.c) an additional homogenization step.

In an alternative embodiment, all or a part of the additional ingredients, such as aroma, may be added already between the third or fourth step.

Preferably, step 8 is divided into:
a) a step 8.a, wherein the mixture is pre-heated to 70-100° C., preferably 85-95° C., e.g. for 2-5 minutes;
b) a step 8.b, wherein the mixture is heated to 130-145° C., preferably to 139-141° C., e.g. for 6-15 seconds; and
c) a step 8.c, wherein the mixture is homogenized at a pressure of 40-200 bar; preferably step 8.c is carried out at less than 90° C.

Dose Unit and Daily Dose

The nutritional compositions herein are typically provided in a dose unit.

A dose unit herein refers to 100-200 mL, preferably 100-150 mL, preferably provided in package such as a bottle, tetra brick or bag.

Such a dose unit provides 300-500 kcal, preferably 350-450 kcal.

Such a dose unit provides 14-40 g, preferably 15-30 g, more preferably 18-22 g of protein, such as 20 g of protein.

An exemplary dose unit provides 400 kcal and 20 g of protein in 125 mL.

An exemplary daily dose for complete nutrition of, e.g., 1500-2500 kcal of the nutritional compositions herein may be provided by 3-8 dose units, preferably by 5 dose units. For example, a daily dose for complete nutrition may be provided by 5 dose units each providing 350-450 kcal.

A typical daily dose for supplemental nutrition of, e.g., 300-900 kcal of the nutritional compositions herein may be provided by 1-3 dose units, preferably by 1 or 2 dose units, for example by 1 or 2 dose units each providing 350-450 kcal.

EMBODIMENTS

Embodiment 1: PUFA, vitamin E, vitamin D and the protein bound amino acids glycine, arginine and tryptophan as active ingredients for use in therapy of patients with sarcopenia and/or frailty or pre-sarcopenic and/or pre-frail patients,
wherein an effective amount of said active ingredients is administered in the form of a nutritional composition comprising
a) a lipid component providing 40-50 EN % based on the total energy of the nutritional composition, wherein 12-16 EN % based on the total energy of the nutritional composition is provided by PUFA,
b) 4.0-8.0 mg/100 mL alpha-TE vitamin E,
c) 5.0-12.0 μg/100 mL vitamin D,
d) 2.5-4.5 g/100 mL glycine,
e) 0.5-1.5 g/100 mL arginine, and
f) at least 0.02 g/100 mL tryptophan.

Embodiment 2: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to the preceding embodiment, wherein the nutritional composition has a caloric density of at least 2.0 kcal/mL, preferably at least 2.5 kcal/mL, more preferably at least 2.6 kcal/mL, even more preferably at least 2.8 kcal/mL, even more preferably at least 3.0 kcal/mL, even more preferably at least 3.1 kcal/mL.

Embodiment 3: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the nutritional composition has a caloric density of 2.0-5.0 kcal/mL, preferably 2.5-4.0 kcal/mL, more preferably 2.6-3.8 kcal/mL, even more preferably 2.8-3.6 kcal/mL, even more preferably 3.0-3.4 kcal/mL, even more preferably 3.1-3.3 kcal/mL.

Embodiment 4: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the lipid component comprises rapeseed oil and/or canola oil, preferably rapeseed oil, also preferably canola oil.

Embodiment 5: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the nutritional composition comprises at least 10 wt %, preferably at least 12 wt %, more preferably at least 13 wt % of protein based on the total weight of the nutritional composition.

Embodiment 6: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the nutritional composition comprises at least 14 g, for example 14-20 g, preferably at least 15 g, for example 15-18 g, more preferably at least 15.5 g, for example 15.5-17.0 g, most preferably at least 16 g of protein per 100 mL of the nutritional composition.

Embodiment 7: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the protein component provides at least 15 EN %, for example 15-25 EN %, preferably at least 18 EN %, for example 18-22 EN %, more preferably at least 19 EN %, for example 19-21 EN %, based on the total energy of the nutritional composition.

Embodiment 8: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the protein to water ratio is at least 2.0/10 [g/g], more preferably at least 2.5/10 [g/g].

Embodiment 9: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the nutritional composition further comprises a carbohydrate component providing at least 20 EN %, preferably 30-40 EN %, more preferably 33-37 EN %, for example 34-36 EN % based on the total energy of the nutritional composition.

Embodiment 10: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein
the protein component provides 15-25 EN % based on the total energy of the nutritional composition, and wherein the nutritional composition further comprises
a carbohydrate component providing 30-40 EN % based on the total energy of the nutritional composition.

Embodiment 11: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein
the protein component provides 18-22 EN %, preferably 19-21 EN % based on the total energy of the nutritional composition,
the lipid component provides 43-47 EN %, preferably 44-46 EN % based on the total energy of the nutritional composition, and wherein the nutritional composition further comprises a carbohydrate component providing 33-37 EN %, preferably 34-36 EN % based on the total energy of the nutritional composition.

Embodiment 12: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein 24-32 EN % based on the total energy of the nutritional composition is provided by MUFA, and 1-5 EN % based on the total energy of the nutritional composition is provided by SFA.

Embodiment 13: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein
- 13-15 EN % based on the total energy of the nutritional composition is provided by PUFA,
- 26-30 EN %, for example 28 EN %, based on the total energy of the nutritional composition is provided by MUFA, and
- 2-4 EN %, for example 3 EN %, based on the total energy of the nutritional composition is provided by SFA.

Embodiment 14: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the nutritional composition comprises 4.5-7.0 mg/100 mL alpha-TE vitamin E, preferably 5.0-6.5 mg/100 mL alpha-TE vitamin E, more preferably 5.2-6.2 mg/100 mL alpha-TE vitamin E, even more preferably 5.5-6.0 mg/100 mL alpha-TE vitamin E.

Embodiment 15: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the nutritional composition comprises 6.0-10.5 µg/100 mL vitamin D, preferably 7.0-9.5 µg/100 mL vitamin D, more preferably 7.2-9.0 µg/100 mL vitamin D, even more preferably 7.5-8.5 µg/100 mL vitamin D.

Embodiment 16: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the nutritional composition further comprises proline, preferably 1.5-4.0 g/100 mL proline, more preferably 2.0-3.0 g/100 mL proline, even more preferably 2.2-2.6 g/100 mL proline.

Embodiment 17: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the nutritional composition further comprises cysteine, preferably at least 0.01 g/100 mL cysteine, more preferably 0.01-0.1 g/100 mL cysteine, even more preferably 0.02-0.05 g/100 mL cysteine.

Embodiment 18: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the protein component comprises hydrolysed collagen.

Embodiment 19: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the protein component comprises a protein source selected from vegetable proteins, animal proteins other than collagen and mixtures thereof, for example milk protein, soy protein, pea protein, egg white and hydrolysates thereof.

Embodiment 20: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the protein component comprises a protein source selected from milk proteins, such as total milk protein, milk protein isolate, milk protein concentrate, whey, casein and mixtures thereof.

Embodiment 21: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the protein component comprises at least two different protein sources.

Embodiment 22: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the protein component comprises collagen hydrolysate as a first protein source and milk protein as a second protein source.

Embodiment 23: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the nutritional composition further comprises B vitamins, preferably at least 5 mg/100 mL B vitamins, more preferably 6-20 mg/100 mL B vitamins, even more preferably 7-12 mg/100 mL B vitamins.

Embodiment 24: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the nutritional composition further comprises calcium, preferably 50-300 mg/100 mL calcium, more preferably 120-200 mg/100 mL calcium, even more preferably 150-175 mg/100 mL calcium.

Embodiment 25: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the nutritional composition is an emulsion, preferably an oil-in-water (O/W) emulsion.

Embodiment 26: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the nutritional composition has a pH of 5.5-9.0, preferably 7.0-9.0, for example 6-9 or 7-8.

Embodiment 27: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the nutritional composition has a viscosity of 50-900 mPas, preferably 200-750 mPas, determined at a shear rate of $\gamma=1s^{-1}$ at 20° C.

Embodiment 28: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the nutritional composition is nutritionally complete.

Embodiment 29: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the nutritional composition is administered orally.

Embodiment 30: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the patients are elderly patients (age>65) having a BMI of <22 kg/m2, preferably <20 kg/m2, more preferably <18.5 kg/m2, even more preferably <17 kg/m2, even more preferably <16 kg/m2.

Embodiment 31: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the patients are elderly patients (age≥65) having an FFMI of <16 kg/m2, preferably <15 kg/m2, more preferably <14 kg/m2, even more preferably <13 kg/m2, if they are female, and having an FFMI of <18 kg/m2, preferably <17 kg/m2, more preferably <16 kg/m2, even more preferably <15 kg/m2, if they are male.

Embodiment 32: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the nutritional composition is used in the prevention or treatment of malnutrition, preferably protein malnutrition, also preferably protein-energy malnutrition (PEM).

Embodiment 33: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the nutritional composition is used in the prevention or treatment of nutrient deficiencies associated with malnutrition, preferably protein malnutrition, also preferably protein-energy malnutrition (PEM).

Embodiment 34: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the nutritional composition is provided in a dose unit of 100-200 mL, preferably 100-150 mL.

Embodiment 35: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the nutritional composition is provided in a dose unit providing 300-500 kcal, preferably 350-450 kcal.

Embodiment 36: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the nutritional composition is provided in a dose unit providing 15-30 g, preferably 18-22 g of protein.

Embodiment 37: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the nutritional composition is provided in a dose unit of 125 mL providing 400 kcal and 20 g of protein.

Embodiment 38: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the nutritional composition is administered in 3-8 dose units as defined in any of embodiments 34-37 daily, preferably 5 dose units daily, for example 5 dose units daily each providing 350-450 kcal, or for example 5 dose units daily each providing 18-22 g of protein.

Embodiment 39: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the nutritional composition is administered in 1-3 dose units as defined in any of embodiments 34-37 daily, preferably 1 or 2 dose units daily, for example 1 or 2 dose units daily each providing 350-450 kcal, or for example 1 or 2 dose units daily each providing 18-22 g of protein.

Embodiment 40: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the nutritional composition is administered in a daily dose of 1500-2500 kcal.

Embodiment 41: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the nutritional composition is administered in a daily dose of 300-900 kcal.

Embodiment 42: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the nutritional composition is administered in a daily dose of 75-125 g of protein.

Embodiment 43: PUFA, vitamin E, vitamin D and the protein bound amino acids glycine, arginine and tryptophan as active ingredients for use in therapy of patients with sarcopenia and/or frailty or pre-sarcopenic and/or pre-frail patients according to any of the preceding embodiments, wherein the nutritional composition is administered in a daily dose of 15-45 g of protein.

Embodiment 44: Nutritional composition comprising
a) a lipid component providing 40-50 EN % based on the total energy of the nutritional composition, wherein 12-16 EN % based on the total energy of the nutritional composition is provided by PUFA,
b) 4.0-8.0 mg/100 mL alpha-TE vitamin E,
c) 5.0-12.0 µg/100 mL vitamin D,
d) 2.5-4.5 g/100 mL glycine,
e) 0.5-1.5 g/100 mL arginine, and
f) at least 0.02 g/100 mL tryptophan.

Embodiment 45: Nutritional composition according to the preceding embodiment having a caloric density of at least 2.0 kcal/mL, preferably at least 2.5 kcal/mL, more preferably at least 2.6 kcal/mL, even more preferably at least 2.8 kcal/mL, even more preferably at least 3.0 kcal/mL, even more preferably at least 3.1 kcal/mL.

Embodiment 46: Nutritional composition according to any of the preceding embodiments having a caloric density of 2.0-5.0 kcal/mL, preferably 2.5-4.0 kcal/mL, more preferably 2.6-3.8 kcal/mL, even more preferably 2.8-3.6 kcal/mL, even more preferably 3.0-3.4 kcal/mL, even more preferably 3.1-3.3 kcal/mL.

Embodiment 47: Nutritional composition according to any of the preceding embodiments, wherein the lipid component comprises rapeseed oil and/or canola oil, preferably rapeseed oil, also preferably canola oil.

Embodiment 48: Nutritional composition according to any of the preceding embodiments comprising at least 10 wt %, preferably at least 12 wt %, more preferably at least 13 wt % of protein based on the total weight of the nutritional composition.

Embodiment 49: Nutritional composition according to any of the preceding embodiments comprising at least 14 g, for example 14-20 g, preferably at least 15 g, for example 15-18 g, more preferably at least 15.5 g, for example 15.5-17.0 g, most preferably at least 16 g of protein per 100 mL of the nutritional composition.

Embodiment 50: Nutritional composition according to any of the preceding embodiments, wherein the protein component provides at least 15 EN %, for example 15-25 EN %, preferably at least 18 EN %, for example 18-22 EN %, more preferably at least 19 EN %, for example 19-21 EN %, based on the total energy of the nutritional composition.

Embodiment 51: Nutritional composition according to any of the preceding embodiments, wherein the protein to water ratio is at least 2.0/10 [g/g], more preferably at least 2.5/10 [g/g].

Embodiment 52: Nutritional composition according to any of the preceding embodiments further comprising a carbohydrate component providing at least 20 EN %, preferably 30-40 EN %, more preferably 33-37 EN %, for example 34-36 EN % based on the total energy of the nutritional composition.

Embodiment 53: Nutritional composition according to any of the preceding embodiments, wherein
the protein component provides 15-25 EN % based on the total energy of the nutritional composition, and which nutritional composition further comprises
a carbohydrate component providing 30-40 EN % based on the total energy of the nutritional composition.

Embodiment 54: Nutritional composition according to any of the preceding embodiments, wherein
the protein component provides 18-22 EN %, preferably 19-21 EN % based on the total energy of the nutritional composition,
the lipid component provides 43-47 EN %, preferably 44-46 EN % based on the total energy of the nutritional composition, and which nutritional composition further comprises
a carbohydrate component providing 33-37 EN %, preferably 34-36 EN % based on the total energy of the nutritional composition.

Embodiment 55: Nutritional composition according to any of the preceding embodiments, wherein 24-32 EN % based on the total energy of the nutritional composition is provided by MUFA, and 1-5 EN % based on the total energy of the nutritional composition is provided by SFA.

Embodiment 56: Nutritional composition according to any of the preceding embodiments, wherein
13-15 EN % based on the total energy of the nutritional composition is provided by PUFA,
26-30 EN %, for example 28 EN %, based on the total energy of the nutritional composition is provided by MUFA, and
2-4 EN %, for example 3 EN %, based on the total energy of the nutritional composition is provided by SFA.

Embodiment 57: Nutritional composition according to any of the preceding embodiments comprising 4.5-7.0 mg/100 mL alpha-TE vitamin E, preferably 5.0-6.5 mg/100 mL alpha-TE vitamin E, more preferably 5.2-6.2 mg/100 mL alpha-TE vitamin E, even more preferably 5.5-6.0 mg/100 mL alpha-TE vitamin E.

Embodiment 58: Nutritional composition according to any of the preceding embodiments comprising 6.0-10.5 µg/100 mL vitamin D, preferably 7.0-9.5 µg/100 mL vitamin D, more preferably 7.2-9.0 µg/100 mL vitamin D, even more preferably 7.5-8.5 µg/100 mL vitamin D.

Embodiment 59: Nutritional composition according to any of the preceding embodiments further comprising proline, preferably 1.5-4.0 g/100 mL proline, more preferably 2.0-3.0 g/100 mL proline, even more preferably 2.2-2.6 g/100 mL proline.

Embodiment 60: Nutritional composition according to any of the preceding embodiments further comprising cysteine, preferably at least 0.01 g/100 mL cysteine, more preferably 0.01-0.1 g/100 mL cysteine, even more preferably 0.02-0.05 g/100 mL cysteine.

Embodiment 61: Nutritional composition according to any of the preceding embodiments, wherein the protein component comprises hydrolysed collagen.

Embodiment 62: Nutritional composition according to any of the preceding embodiments, wherein the protein component comprises a protein source selected from vegetable proteins, animal proteins other than collagen and mixtures thereof, for example milk protein, soy protein, pea protein, egg white and hydrolysates thereof.

Embodiment 63: Nutritional composition according to any of the preceding embodiments, wherein the protein component comprises a protein source selected from milk proteins, such as total milk protein, milk protein isolate, milk protein concentrate, whey, casein and mixtures thereof.

Embodiment 64: Nutritional composition according to any of the preceding embodiments, wherein the protein component comprises at least two different protein sources.

Embodiment 65: Nutritional composition according to any of the preceding embodiments, wherein the protein component comprises collagen hydrolysate as a first protein source and milk protein as a second protein source.

Embodiment 66: Nutritional composition according to any of the preceding embodiments further comprising B vitamins, preferably at least 5 mg/100 mL B vitamins, more preferably 6-20 mg/100 mL B vitamins, even more preferably 7-12 mg/100 mL B vitamins.

Embodiment 67: Nutritional composition according to any of the preceding embodiments further comprising calcium, preferably 50-300 mg/100 mL calcium, more preferably 120-200 mg/100 mL calcium, even more preferably 150-175 mg/100 mL calcium.

Embodiment 68: Nutritional composition according to any of the preceding embodiments being an emulsion, preferably an oil-in-water (O/W) emulsion.

Embodiment 69: Nutritional composition according to any of the preceding embodiments having a pH of 5.5-9.0, preferably 7.0-9.0, for example 6-9 or 7-8.

Embodiment 70: Nutritional composition according to any of the preceding embodiments having a viscosity of 50-900 mPas, preferably 200-750 mPas, determined at a shear rate of $\gamma=1s^{-1}$ at 20° C.

Embodiment 71: Nutritional composition according to any of the preceding embodiments which is nutritionally complete.

Embodiment 72: Dose unit comprising the nutritional composition as defined in any of embodiments 1-71.

Embodiment 73: Dose unit according to embodiment 72 comprising 100-200 mL, preferably 100-150 mL of the nutritional composition, preferably provided in package such as a bottle, tetra brick or bag.

Embodiment 74: Dose unit according to embodiment 72 or 73 providing 300-500 kcal, preferably 350-45 kcal.

Embodiment 75: Dose unit according to any of embodiments 72-74 providing 15-30 g, preferably 18-22 g of protein.

Embodiment 76: Dose unit according to any of embodiments 72-75 providing 400 kcal and 20 g of protein in 125 mL.

Embodiment 77: Dosage regime for use in (nutritional) therapy of patients with sarcopenia and/or frailty or pre-sarcopenic and/or pre-frail patients, wherein a daily dose for complete nutrition is provided by 3-8 dose units as defined in any of embodiments 72-76, preferably by 5 dose units, for example by 5 dose units each providing 350-450 kcal.

Embodiment 78: Dosage regime according to embodiment 77, wherein the daily dose for complete nutrition is 1500-2500 kcal.

Embodiment 79: Dosage regime for use in (nutritional) therapy of patients with sarcopenia and/or frailty or pre-sarcopenic and/or pre-frail patients, wherein a daily dose for supplemental nutrition is provided by 1-3 dose units as defined in any of embodiments 72-76, preferably by 1 or 2 dose units, for example by 1 or 2 dose units each providing 350-450 kcal.

Embodiment 80: Dosage regime according to embodiment 79, wherein the daily dose for supplemental nutrition is 300-900 kcal.

EXAMPLES

The nutritional composition according to Table 1 was prepared by mixing and homogenization.

Surprisingly, high caloric densities could be reached by adding collagen hydrolysate in sufficient amounts to milk protein.

The Example (Table 1) further shows that with inclusion of sufficient amounts of collagen hydrolysate very high energy densities of protein could be reached in a formula that provides very high caloric density (3.2 kcal/mL).

The inventors further observed that fouling during heat treatment could be reduced/prevented when sufficient amounts of collagen hydrolysate were used in the protein component. Advantages observed with the nutritional composition according to Table 1 include an improved stability against subsequent UHT (no fouling), an improved viscosity and an improved shelf life (at least 6 months).

With the nutritional composition, a drinkable viscosity of a nutritionally complete composition can be provided in spite of a high protein and energy content.

The inventors further observed that bitterness of the product could be reduced by increasing wt % of collagen hydrolysate in the protein component. Therefore, the nutritional composition will result in a better patient compliance.

Trials

Trials 1 and 2

The nutritional composition according to Table 1 (herein referred to as "test drink") was given to 20 subjects with an indication for supplemental nutrition of approx. 400 kcal per day. Subjects belong to the age group of 65 and older. The dosage was one bottle of 125 mL per day for seven consecutive days. One such bottle provides 400 kcal, including 20 g protein (20 EN %), 20 g fat (45 EN %) and 35 g carbohydrates (35 EN %). 14 EN % is provided by PUFA.

Adverse effects were documented. Gastrointestinal tolerance parameters were documented. Moreover, (protein) energy intake, compliance (in particular time until full consumption of the test drink and/or amount consumed within 1 hour) and palatability were documented.

Trial 1

8 males and 12 females participated in the study. The test drink was administered in a single dose (125 mL).

All 20 subjects completed the 7 days of intervention. In total, 96% of the prescribed test drinks were consumed. All study participants ingested the test drink within one hour.

Gastrointestinal (GI) symptoms were comparable at baseline and at the end of the 7 day supplementation period. No severe GI symptoms were observed. 11 of the 20 subjects did not report any GI symptoms during the entire study.

The palatability assessment showed a very high acceptance of the test drink. The majority of the subjects rated smell, taste and appearance as 'good' at the start and at the end of the study. No rating of poor or unacceptable was observed. Furthermore, there was no appearance of taste fatigue, even though only one flavor was provided throughout the study.

The results of the palatability assessment (overall opinion) are as follows:

| | | Palatability (overall opinion) | | | | |
|---|---|---|---|---|---|---|
| | | Excellent | Good | Fair | Poor | Unacceptable |
| Observations (Number of study participants) | Study day 1 | 3 | 13 | 4 | 0 | 0 |
| | Study day 7 | 3 | 10 | 7 | 0 | 0 |

The results of the taste assessment are as follows:

| | | Taste | | | | |
|---|---|---|---|---|---|---|
| | | Excellent | Good | Fair | Poor | Unacceptable |
| Observations (Number of study participants) | Study day 1 | 4 | 12 | 4 | 0 | 0 |
| | Study day 7 | 2 | 13 | 5 | 0 | 0 |

In conclusion, the test drink administered in a single dose was well-accepted. The test drink showed good tolerability and palatability resulting in excellent compliance.

Trial 2

9 males and 11 females participated in the study. The test drink was administered in three doses (about 40 mL each).

All 20 subjects completed the 7 days of intervention. In total, 95% of the prescribed test drinks were consumed. All study participants ingested the test drink immediately after handout.

Gastrointestinal (GI) symptoms were comparable at baseline and at the end of the 7 day supplementation period. No severe GI symptoms were observed. 13 of the 20 subjects did not report any GI symptoms during the entire study.

Palatability was rated as excellent or good by the majority of the subjects. No rating of poor or unacceptable was observed. Furthermore, there was no appearance of taste fatigue, even though only one flavor was provided throughout the study. Perception of sweetness was rated as just right by the majority of the subjects.

The results of the palatability assessment (overall opinion) are as follows:

|  |  | Palatability (overall opinion) | | | | |
| --- | --- | --- | --- | --- | --- | --- |
|  |  | Excellent | Good | Fair | Poor | Unacceptable |
| Observations (Number of study participants) | Study day 1 | 3 | 13 | 4 | 0 | 0 |
|  | Study day 7 | 1 | 16 | 3 | 0 | 0 |

The results of the sweetness assessment are as follows:

|  |  | Sweetness | | | | |
| --- | --- | --- | --- | --- | --- | --- |
|  |  | Extremely sweet | Highly Sweet | Just right | Slightly sweet | Not sweet at all |
| Observations (Number of study participants) | Study day 1 | 0 | 3 | 12 | 4 | 0 |
|  | Study day 7 | 0 | 2 | 17 | 1 | 0 |

In conclusion, the test drink administered in three doses was well-accepted. The test drink showed good tolerability and palatability resulting in excellent compliance.

Trial 3

An in vitro study is conducted to demonstrate the efficacy of a combination of PUFA, vitamin E, vitamin D and the amino acids glycine, arginine and tryptophan. The ability of this combination to rescue the atrophy induced by tumor necrosis factor-alpha (TNF-alpha) as well as its ability to increase protein synthesis is investigated. TNF-alpha levels increase with age, and increased TNF-alpha levels are connected to muscle atrophy and sarcopenia, see e.g. FASEB J. 2005, 19(6), 668-670 (Phillips et al.). Human primary myoblasts are used as cells. Linoleic acid (n-6 PUFA) and alpha-linolenic acid (n-3 PUFA) are used as PUFA. Readouts include myotube differentiation and size (width and area), protein synthesis, and fusion index.

Trial 4

An in vivo study on sarcopenia is conducted in aged rats to demonstrate the efficacy of the nutritional composition of the invention. Readouts include grip strength and muscle force. The in vivo study is carried out in an analogous manner as described in Exp. Gerontol. 2017, 98, 177-183 (Liao et al.).

Trial 5

An in vivo study on muscle protein synthesis is conducted in humans to demonstrate the efficacy of the nutritional composition according to Table 1 (herein referred to as "test drink"). Its efficacy on muscle protein synthesis is investigated using a unilateral leg exercise model. The study involves unilateral leg exercise and bilateral muscle biopsies before and after exercise. The test drink is ingested orally (shortly after exercise). Muscle protein synthesis is quantified using $^{13}C_6$ phenylalanine labeling. $^{13}C_6$ phenylalanine is added to the nutritional composition of the invention (shortly before ingestion).

Methods

Determination of Molecular Weight of the Hydrolysed Collagen by GPC/HPLC

Equipment: GPV/HPLC with UV detector operating at 214 nm. Column: TSK 2000 SW XL (Toshoh Biosience GmbH). Isocratic elution using 400 mmol/l sodium phosphate buffer (pH 5.3). Calibration by means of well-defined Type I-collagen fragments (FILK, Freiburg, Germany). The collagen hydrolysate used in the examples had an average molecular weight of 2 kDa. In general, the skilled person is well aware of molecular weight determination via GPC. Another suitable method for determining the $M_w$ of small macromolecules such as the hydrolysates described herein is MALDI-MS.

TABLE 1

| Protein: | 20 EN % |
| --- | --- |
| Collagen hydrolysate 80% | 16 g/100 mL |
| Milk protein 20% | |
| (Refit 10.8%/MPC-80 9.2%) | |
| glycine* | 3.42 g/100 mL |
| arginine* | 1.05 g/100 mL |
| tryptophan* | 0.05 g/100 mL |
| proline* | 2.38 g/100 mL |
| cysteine* | 0.03 g/100 mL |
| Fat: | 45 EN % |
| Rapeseed oil | 16 g/100 mL |
| of which SFA | 3 EN % |
|  | 1.1 g/100 mL |
| of which MUFA | 28 EN % |
|  | 9.9 g/100 mL |
| of which PUFA | 14 EN % |
|  | 5.0 g/100 mL |
| CHO | 35 EN % |
|  | 28 g/100 mL |
| Caloric density | 3.2 kcal/mL |
| Water | 56 mL/100 mL |
| FSMP balanced** | yes |
| Vitamin D3 | 8 µg/100 mL |
| Vitamin E | 5.67 mg/100 mL (alpha-TE) |

*Bound in collagen hydrolysate or milk protein
**Nutritionally complete in vitamins and minerals

TABLE 2

| Vitamins | | |
| --- | --- | --- |
|  | Minimum per 100 kcal | Maximum per 100 kcal |
| Vitamin A (µg RE) | 35 | 180 |
| Vitamin D (µg) | 0.5 | 3 |
| Vitamin K (µg) | 3.5 | 20 |
| Vitamin C (mg) | 2.2 | 22 |
| Thiamin (mg) | 0.06 | 0.5 |
| Riboflavin (mg) | 0.08 | 0.5 |
| Vitamin B6 (mg) | 0.08 | 0.5 |
| Niacin (mg EN) | 0.9 | 3 |
| Folic acid (µg) | 10 | 50 |
| Vitamin B12 (µg) | 0.07 | 0.7 |

TABLE 2-continued

Vitamins

|  | Minimum per 100 kcal | Maximum per 100 kcal |
|---|---|---|
| Pantothenic acid (mg) | 0.15 | 1.5 |
| Biotin (µg) | 0.75 | 7.5 |
| Vitamin E (mg α-TE) | 0.5 | 3 |

TABLE 3

Minerals

|  | Minimum per 100 kcal | Maximum per 100 kcal |
|---|---|---|
| Sodium (mg) | 30 | 175 |
| Chloride (mg) | 30 | 175 |
| Potassium (mg) | 80 | 295 |
| Calcium (mg) | 35 | 250 |
| Phosphorus (mg) | 30 | 80 |
| Magnesium (mg) | 7.5 | 25 |
| Iron (mg) | 0.5 | 2.0 |
| Zinc (mg) | 0.5 | 1.5 |
| Copper (µg) | 60 | 500 |
| Iodine (µg) | 6.5 | 35 |
| Selenium (µg) | 2.5 | 10 |
| Manganese (mg) | 0.05 | 0.5 |
| Chromium (µg) | 1.25 | 15 |
| Molybdenum (µg) | 3.5 | 18 |
| Fluoride (mg) | — | 0.2 |

The invention claimed is:

1. A nutritional composition comprising components as follows:
   a) a lipid component providing 40-50% contribution of nutritional energy ("EN %") based on the total energy of the nutritional composition, of which 2-4 EN % is provided by saturated fatty acids, 12-16 EN % is provided by polyunsaturated fatty acids ("PUFA"), and 26-30 EN % is provided by monounsaturated fatty acids, based on the total energy of the nutritional composition;
   b) 4.0-8.0 mg/100 mL alpha-tocopherol equivalents ("alpha-TE") vitamin E,
   c) 5.0-12.0 µg/100 mL vitamin D3,
   d) 2.5-4.5 g/100 mL glycine,
   e) 0.5-1.5 g/100 mL arginine,
   f) at least 0.02 g/100 mL tryptophan,
   g) 2.2-2.6 g/100 mL proline, and
   h) 0.02-0.05 g/100 mL cysteine;
   i) a protein component comprising collagen hydrolysate and milk protein, wherein the protein component provides at least 15 EN % based on the total energy of the nutritional composition;
   j) a carbohydrate component providing at least 20 EN % based on the total energy of the nutritional composition;
   k) calcium 150-175 mg/100 mL;
   l) zinc 3.0-4.0 mg/100 mL;
   m) copper 480-540 µg/100 mL;
   n) selenium 20-25 µg/100 mL;
   o) Vitamin B6 0.55-0.62 mg/100 mL;
   p) Vitamin B12 1.0-1.2 µg/100 ml;
   q) Folic acid 60-75 µg/100 mL;
   r) Vitamin C 35-50 mg/100 mL;
   s) water; and
   wherein the glycine, arginine, tryptophan, proline and cysteine are those bound in the collagen hydrolysate and/or the milk protein.

2. The nutritional composition of claim 1,
   wherein the composition comprises the components in the EN % and in the amount values listed in the following table:

| Protein: | 20 EN % |
|---|---|
| Collagen hydrolysate 80% Milk protein 20% | 16 g/100 mL |
| glycine | 3.42 g/100 mL |
| arginine | 1.05 g/100 mL |
| tryptophan | 0.05 g/100 mL |
| proline | 2.38 g/100 mL |
| cysteine | 0.03 g/100 mL |
| Fat: | 45 EN % |
| Rapeseed oil | 16 g/100 mL |
| of which SFA | 3 EN % |
|  | 1.1 g/100 mL |
| of which MUFA | 28 EN % 9.9 g/100 mL |
| of which PUFA | 14 EN % |
|  | 5.0 g/100 mL |
| CHO | 35 EN % |
|  | 28 g/100 mL |
| Caloric density | 3.2 kcal/mL |
| Water | 56 mL/100 mL |
| Vitamin D3 | 8 µg/100 mL |
| Vitamin E | 5.67 mg/l00 mL (alpha-TE) | wherein said nutritional composition is nutritionally complete in vitamins and minerals ("FSMP balanced"), and wherein said nutritional composition has a caloric density of at least 3.2 kcal/mL.

3. The nutritional composition of claim 1, wherein the nutritional composition has a caloric density of at least 2.0 kcal/mL.

4. The nutritional composition of claim 1, wherein the lipid component comprises rapeseed oil and/or canola oil as a lipid source for the polyunsaturated fatty acids, the saturated fatty acids, and the monounsaturated fatty acids.

5. The nutritional composition of claim 1, wherein the protein component provides 18-22 EN % based on the total energy of the nutritional composition;
   wherein the lipid component provides 43-47 EN % based on the total energy of the nutritional composition, and
   wherein the carbohydrate component provides 33-37 EN % based on the total energy of the nutritional composition.

* * * * *